| United States Patent [19] | [11] Patent Number: 4,764,512 |
|---|---|
| Molino et al. | [45] Date of Patent: Aug. 16, 1988 |

[54] BENZODIAZINONE-PYRIDONE COMPOUNDS, CARDIOTONIC COMPOSITIONS INCLUDING THE SAME, AND THEIR USES

[75] Inventors: Bruce F. Molino; Henry F. Campbell, both of Lansdale; Donald E. Kuhla, Doylestown; William L. Studt, Harleysville, all of Pa.

[73] Assignee: Rorer Pharmaceutical Corporation, Ft. Washington, Pa.

[21] Appl. No.: 900,868

[22] Filed: Aug. 27, 1986

[51] Int. Cl.$^4$ .................. A61K 31/395; C07D 401/10
[52] U.S. Cl. ..................... 514/183; 514/221; 514/248; 514/249; 540/453; 540/461; 540/512; 540/517; 540/524; 544/231; 544/239; 544/249; 546/271

[58] Field of Search ............... 514/183, 221, 248, 249; 540/453, 461, 517, 512, 524; 544/231, 239, 249; 546/271

[56] References Cited

U.S. PATENT DOCUMENTS 4,666,913 5/1987 Kubla et al. .................. 514/221

Primary Examiner—Robert T. Bond
Attorney, Agent, or Firm—James A. Nicholson; Imre (Jim) Balogh

[57] ABSTRACT

This invention relates to substituted benzodiazinone-pyridone compounds and their use as cardiotonic agents including methods for increasing cardiac contractility, pharmaceutical compositions including the same and methods for the preparation thereof.

21 Claims, No Drawings

BENZODIAZINONE-PYRIDONE COMPOUNDS, CARDIOTONIC COMPOSITIONS INCLUDING THE SAME, AND THEIR USES

FIELD OF INVENTION

This invention relates to substituted benzodiazinonepyridones useful as cardiotonic agents for the treatment of congestive heart failure. This invention also relates to methods for increasing cardiac contractility using said compounds, and pharmaceutical compositions including said compounds.

Congestive heart failure is a life-threatening condition in which myocardial contractility is depressed so that the heart is unable to adequately pump the blood returning to it. Normal pathologic sequelae include decreased cardiac output, venous pooling, increased venous pressure, edema, increased heart size, increased myocardial wall tension, and eventually cessation of contractility.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, and amrinone have been used to provide necessary inotropic support for the failing heart.

Cardiotonic agents which are described as having positive inotropic activity include the 5-pyridyl substituted pyridones disclosed in U.S. Pat. Nos.: 4,004,012; 4,072,746; 4,107,315; 4,137,233; 4,199,586; 4,271,168 and 4,107,315; in GB 2070606A; and in PTC published Appl. No. PCT/CH81/00023. Other cardiotonic drugs include the diazacyclic substituted carbostyril compounds disclosed in U.S. Pat. Nos. 4,414,390 and 4,415,572, cardiotonic pyridyl substituted carbostyril compounds disclosed in EPO application Serial No. 84308925.1, and the 5-phenyl-thiazole compounds disclosed in U.S. Pat. No. 4,418,070.

Cardiotonic bicyclic heteroaryl-5-substituted pyridyl compounds are disclosed in PCT published application Serial No. PCT/US83/01285; and, cardiotonic diazheterocyclic-5-substituted pyridyl compounds are disclosed in U.S. Pat. Nos. 4,432,979, 4,514,400 and 4,539,321. Each of the aforementioned is assigned to the same assignee as the present application.

SUMMARY OF THE INVENTION

The present invention relates to a method for increasing cardiac contractility in humans and other mammals comprising the administration of an effective inotropic amount of a benzodiazinone-pyridone compound.

This invention comprises particularly the administration to a patient of an effective inotropic amount of a benzodiazinone-pyridone compound within the scope by Formula I:

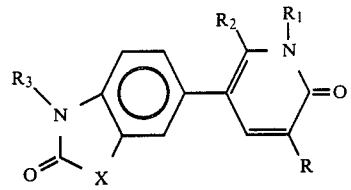

where
R is
   hydrogen
   alkyl
   alkoxyalkyl
   hydroxyalkyl having 1-6 carbon atoms
   halo
   cyano
   carbamoyl
   alkyl carbamoyl
   formyl
   alkyleneamino or
   amino;
X is

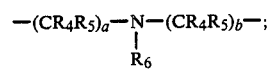

$R_1$, $R_2$, $R_3$, and $R_5$ are
   hydrogen or alkyl;
$R_4$ and $R_6$ are
   hydrogen
   alkyl or
   aralkyl;
a and b are 0, 1 or 2 and a+b=0, 1 or 2;
$R_4$ or $R_5$ groups on vicinal carbon atoms may together form a carbon-carbon double bond; and geminal $R_4$ and $R_5$ groups may together form a spiro substituent, $-(CH_2)_d-$, where d is 2 to 5; or a pharmaceutically acceptable salt thereof.

DETAILED DESCRIPTION

Certain of the compounds encompassed within the present invention, and particularly, compounds of Formula I, may exist in enolic or tautomeric forms, and all of these forms are considered to be included within the scope of this invention.

The compounds of this invention which have particular usefulness as cardiotonic agents are described by formula I wherein the benzodiazinone portion of the molecule is described by one of Formulae II, IIIa, IIIb or IVa-IVc:

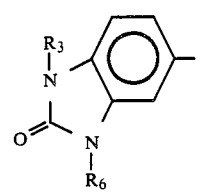

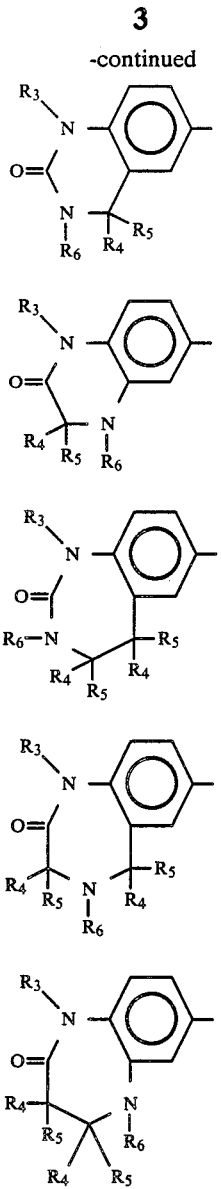

wherein: $R_3$, $R_4$, $R_5$ and $R_6$ are as described above.

A more preferred class of compounds within the present invention includes compounds of Formulae I, II, IIIa and IVa wherein R is cyano, $R_2$ is lower alkyl and $R_1$, $R_4$, $R_5$ and $R_6$ are lower alkyl.

Most preferred compounds are those disclosed by Formula I, wherein R is cyano, Rhd 1 is hydrogen, $R_2$ is methyl and $R_4$, $R_5$ and $R_6$ are hydrogen or methyl.

A special emodiment of the present invention comprises compound of Formula I where $R^4$ and $R^5$ form a spiro ring system, and example, of which is shown by Formula V:

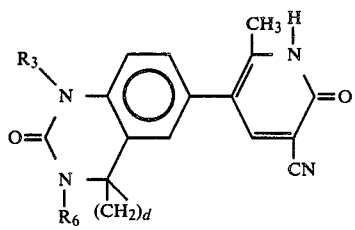

As employed above and throughout the disclosure, the following terms, unless otherwise indicated, shall be understood to have the following meanings:

"Alkyl" means a saturated aliphatic hydrocarbon which may be either straight or branched-chained containing from about 1 to about 6 carbon atoms.

"Lower alkyl" means an alkyl group as above, having 1 to about 4 carbon atoms.

"Alkyl carbamoyl" means a carbamoyl group substituted by one or two alkyl groups. Preferred groups are the lower alkyl carbamoyl groups.

"Hydroxyalkyl" means an alkyl group substituted by a hydroxy group. Hydroxy lower alkyl groups are preferred and include hydroxymethyl, 2-hydroxyethyl, 2-hydroxyproply, and 3-hydroxypropyl.

"Alkoxy" means an alkyl oxy group in which "alkyl" is as previously described. Lower alkoxy groups are preferred and include methoxy, ethoxy, n-propoxy, i-propoxy, secpropoxy, n-butoxy among others.

"Alkoxyalkyl" means an alkyl group as previously described substituted by an alkoxy group as previously described.

"Alkyleneamino" means —$RNH_2$ where —R is alkylene of 1 to about 6 carbon atoms. The preferred groups are the lower alkyleneamino groups which mean amino groups substituted with alkylene groups of 1 to about 4 carbon atoms. The most preferred alkyleneamino group is methyleneamino.

The preferred halo group is chloro.

The preferred aralkyl groups are benzyl or phenethyl.

The compounds of this invention may be useful in the form of the free base, if a basic group is present, in the form of salts and as a hydrate, and all forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Compounds of this invention may be prepared by the following reaction sequences:

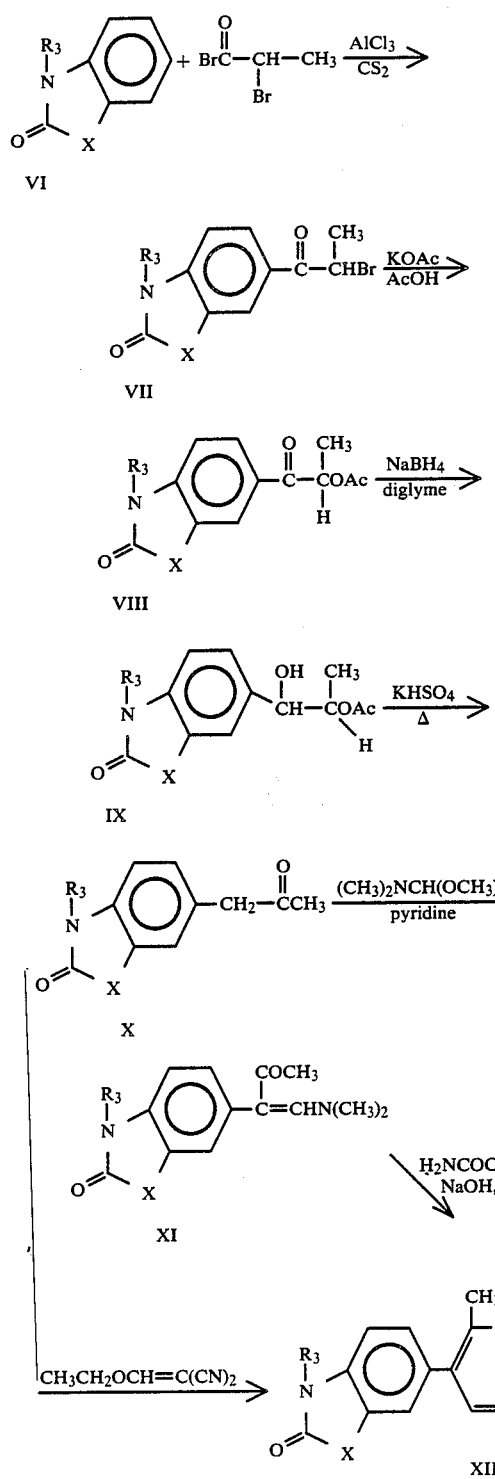

where R₃ is hydrogen or alkyl.

Treatment of a benzodiazinone intermediate VI (when a=o) with an α-halopropiononyl halide under Friedel-Crafts reaction conditions forms the acylation adduct VII. Treatment of this bromo-ketone with potassium acetate in acetic acid with warming results in the replacement of the halo group with an acetoxy group of VIII. When the latter is treated to sodium borohydride reduction the corresponding acetoxy-alcohol of IX is formed. Acid dehydration with potassium bisulfate yields the desired ketone X. Reaction of the ketone with dimethylformamide dimethylacetal (DMF-DMA) with warming followed by treatment, in DMF or the like, with cyanoacetamide in the presence of sodium hydride ring closes to the desired benzodiazinone-pyridone compounds XII.

Reaction of the ketone X with ethoxymethylenemalononitrile following the procedure of Singh [Heterocycles, 23, 1479 (1985)] also results in the desired compounds of XII.

Conversion of the cyano group into other R substituent groups may be accomplished by techniques known in the art.

Treatment of the 1-[H]-pyridone compound with a suitable alkylating agent results in the compound of the present invention wherein R₁ is other than hydrogen.

When R₂ is hydrogen, the starting Friedel-Crafts reaction is carried out with -bromoacetylbromide in place of the proprionyl compound.

The benzodiazinone intermediates VI, particularly the unsubstituted and lower alkyl substituted compounds, are either known compounds or may be prepared in accordance with the reaction sequences described below.

The 3, 4-dihydro-2(1H)-quinazolinone intermediates may be prepared from analogous 2-carbamoyl functionality to the methylene amine. Treatment of the resulting diamine with carbonyldiimidazole in THF affords the 3, 4-dihydro-2(1H)-quinazolinone.

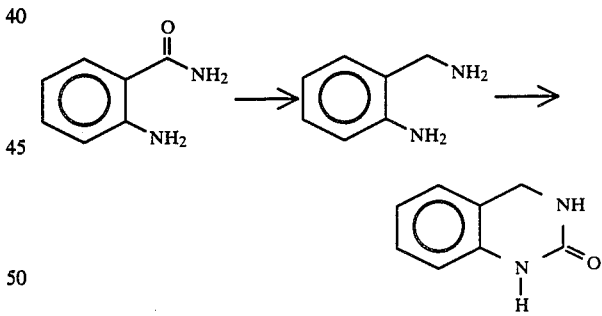

When b=0, a=1 and at least one of R₄ or R₅ is hydrogen in Formula I above and R³ is as described above, the intermediate quinazolinone may be prepared as shown below.

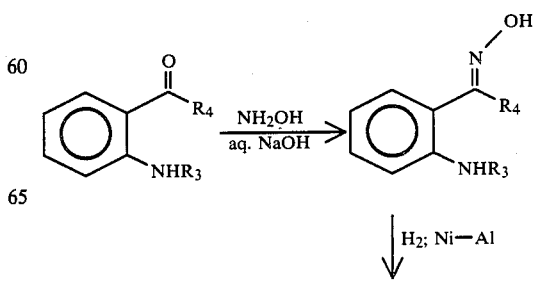

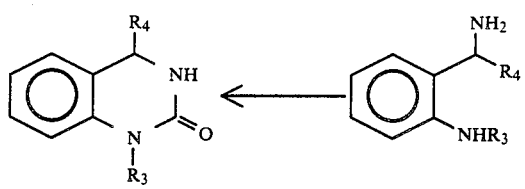

Treatment of 1-R$_4$-(2-R$_3$-substituted aniline)-ketone with hydroxylamine and aqueous sodium hydroxide affords the oxime. Catalytic hydrogenation, preferably using Al-Ni catalyst, results in the amine, which may be cyclized, using carbonyldiimidazole, to the R$_4$-substituted-2-(1H)quinazolinone. When R$_3$ is hydrogen in the above Scheme, the R$_4$ substituted intermediate, may be alkylated selectively in the R$_3$ positions using a hydride reagent in a polar aprotic solvent and an appropriate alkylating reagent, preferably sodium hydride in DMSO.

The prepartion of R$_6$-substituted benzodiazinone intermediates is shown below.

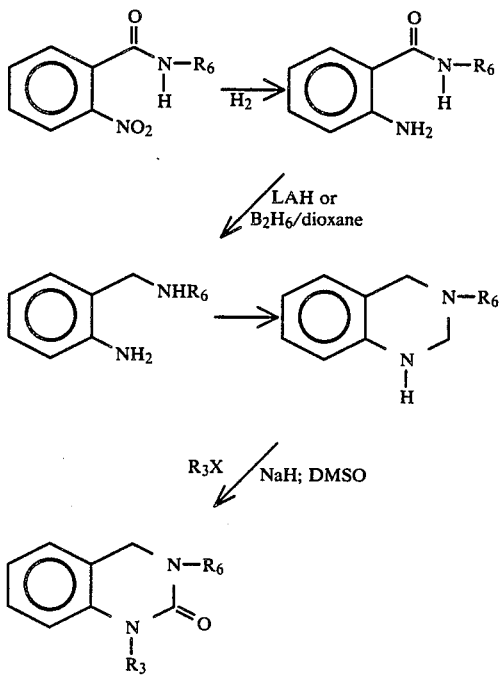

Catalystic hydrogenation of a R$_6$-substituted-2-nitrobenzamide followed by the hydride reduction of the R$_6$-substituted-2-amino-benzamide results in the methylene diamine which may be cyclized to the R$_6$-substituted-2(1H)-quinazolinone. See, M. R. Boots; S. G. Boots; J. Med. Chem., 13, 144(1969). Alkylation of the 1-N position affording R$_3$-substitution may be accomplished at this stage. See, W. E. Coyne and J.W. Cusic, infra. Another method for the preparation of the R$_6$ substituted quinazolinone intermediates involves the rearrangement of a quinazolidinol as reported in Pilicheva, et al., Dokl. Akad. Nauk SSSR (1974), 218(6), 1375–6.

Another method for the preparation of R$_3$-substituted 2H-quinazolinones is described by W. E. Coyne and J. W. Cusik, J. Med. Chem., 11, 1208 (1968), hereby incorporated by reference. Treatment of a 1-N-substituted isatoic anhydride with ammonia affords the 2-substituted amino benzamide, which may be reduced to the diamine and cyclized to the 1-N substituted intermediate as described above. The 3-position may be alkylated to give the 1-R$_3$ - 3-R$_6$-disubstituted intermediate compounds.

The spiro compounds of Formula 1, wherein R$_4$ and R$_5$ together are —(CH$_2$)$_d$—, may be prepared from the 2-nitro styryl intermediate, shown below.

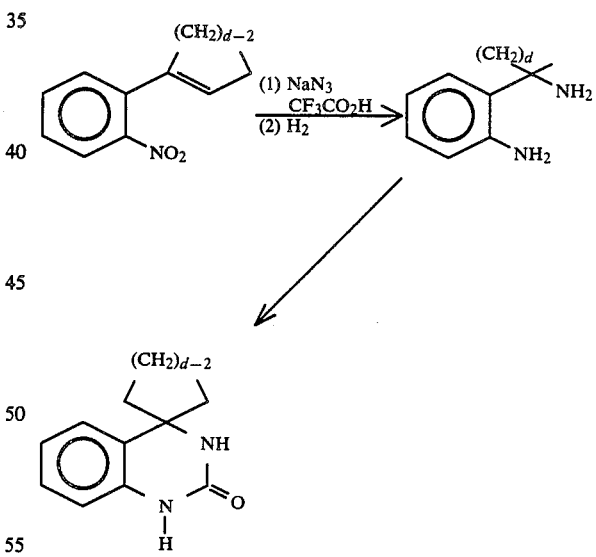

Treatment of the styryl intermediate with sodium azide in trifuloracetic acid, followed by the reduction of the nitro and azido groups results in the diamine intermediate. Cyclization with carbonyl diimidazole results in the spiro benzodiazinone intermediate.

The spiro compounds may also be derived from the 2-amino styryl intermediate, which may be prepared from aniline according to the following Scheme:

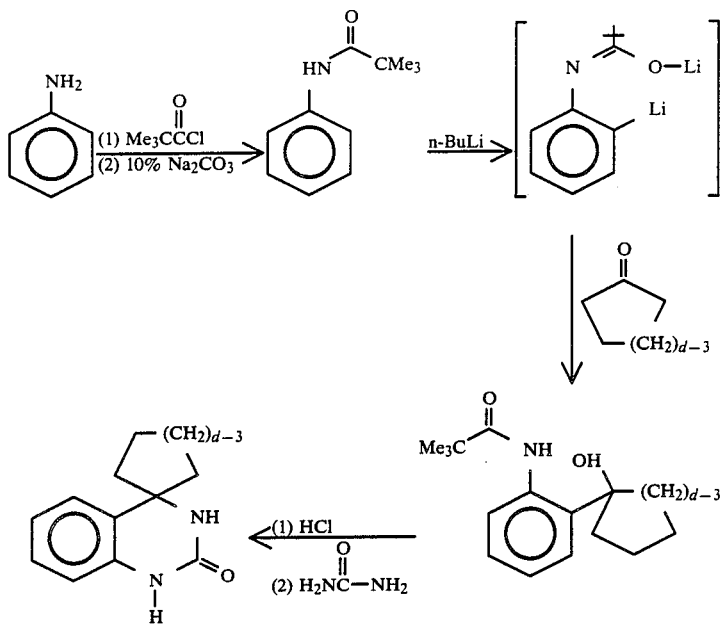

Treatment of aniline with a trialkylacetyl chloride, such as trimethylacetyl chloride, followed by neutralization with 10% aqueous alkali metal carbonate, results in the trialkyl acetamide. Treatment of the amide with n-butyl lithium forms the metallated intermediate, shown above, which is reacted with a carbocyclic ketone, thereby forming the tertiary alcohol intermediate. See H. Gschwend; W. Fuhrer, *J. Org. Chem.*, 44, 1133, (1979). The alcohol may be dehydrated and the amine deprotected in one step by acid hydrolysis using, for example, aqueous hydrochloric acid. Cyclization to the spiro benzodiazinone intermediate may be accomplished by heating a neat mixture of the amine and urea to about 100° to about 200° C. See L. Bernardi et al., *Ger. Offen.*, 1,958,515 (1970), hereby incorporated by reference. Alternatively, the mixture may be heated to cyclization temperatures, about 100° to about 200° C., preferably in an aprotic polar solvent, for about 15 min. to about two days.

The 7-membered benzodiazepinone compounds of Formula I may be prepared according to the following sequence.

the diamine intermediate with carbonyldiimidazole results in the benzodiazepinone intermediate. Either the diamine intermediate, or the benzodiazepinone intermediate may be alkylated, affording the 1- and/or 3-substituted benzodiazepinone compounds.

The quinoxalinone starting materials may be prepared by the N-alkylation of the commerically available 1,2-phenylenediamine with a halo acetic acid (or alkyl ester), such as bromo acetic acid, followed by acid or base treatment to the bicyclic intermediate. For example, when the phenylenediamine is reacted with acrylic acid under acidic conditions, 1,3,4,5-tetrahydro-2-oxo-1,5-benzodia-zepine is formed. This is shown as follows:

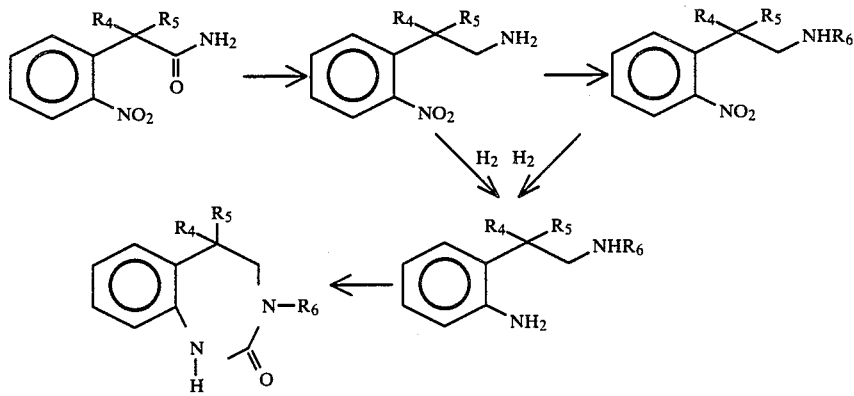

Reduction of the 2-nitrobenzylamide with diborane followed by the catalytic hydrogenation of the nitro group affords the diamine intermediate. Treatment of

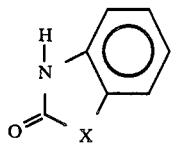

The compounds of Formula I possess positive inotropic activity and are useful as cardiotonic agents in the treatment of humans and other mammals for cardiac disorders including congestive heart failure. The effectiveness of the compounds of this invention as inotropic agents may be determined by the following pharmacologic tests which evaluate the change in cardiac contractile force upon exposure to a dose of said compounds. The ganglionic-beta blocked anesthetized dog procedure is one such standard test procedure; the inotropic results of this procedure generally correlate with the inotropic activity found in human patients.

Ganglionic-Beta Blocked Anesthetized Dog Procedure

Adult mongrel dogs of either sex weighing 10 to 16 kg are fasted overnight, anesthetized with pentobarbital sodium 35 mg/kg, i.v. intubated, respired with room air using a Harvard respirator, and instrumented surgically to monitor myocardial contractile force, heart rate, arterial pressure, aortic flow and EKG limb lead II. The aforesaid measurements are recorded continuously on a strip chart recorder.

Myocardial contractile force is monitored by a Walton-Brodie strain gauge sutured to the left ventricular myocardium parallel to the left anterior descending coronary artery. Arterial pressure is measured using a fluid-filled catheter attached to a pressure transducer introduced via the right femoral artery and positioned in the thoracic aorta. Mean arterial pressure is determined by electronically clamping the pulsatile pressure signal. Aortic flow is monitored using a precalibrated, non-canulating electromagnetic flow probe positioned around the thoracic aorta. Heart rate is monitored using a cardiotachometer triggered by the QRS complex of the limb lead II EKG. The right femoral vein is cannulated for intravenous infusion of drugs. Body temperature is maintained at 37° C.

Following a 30 min postsurgical stabilization period, control values are recorded. Myocardial depression is induced by ganglionic and beta receptor blockade. Initially, the responsiveness of the autonomic nervous system is assessed by performing a 30 sec bilateral carotid occlusion (BCO). Ten minutes later, a saline solution of isoproterenol 0.3 mg/kg, i.v. is administered to assess beta receptor integrity. Ten minutes after that, a saline solution of mecamylamine 2 mg/kg, i.v. is infused, followed by a saline solution of propranolol 1 mg/kg, i.v. plus 0.3 mg/kg/hr. Twenty minutes later, a second BCO is performed to demonstrate ganglionic blockade followed by a second injection of saline isoproterenol 0.3 mg/kg, i.v. to demonstrate beta blockade. Ten minutes later, the test compound or vehicle is administered intravenously in ascending doses at 30 min intervals at 1.5 ml/min in a total volume of 3.5 ml. On completion of the experiment, both BCO and isoproterenol challenges are repeated to verify ganglionic and beta blockade.

The results of the blocked dog test show that compounds of the present invention increase contractile force and heart rate, and aortic blood flow in a dose related manner while maintaining arterial pressure.

Additional test procedures which have been found to be an efficient means for ascertaining the inotropic activity of the compounds of this invention are described below.

Guinea Pig Atria Inotropic Screening Concentrations

Guinea pigs are stunned by a sudden blow to the head; their chests are opened and hearts excised and placed in Kreb's medium (concentrations, mM: NaCl, 118.39; KCl, 4.70; $MgSO_4$, 1.18; $KH_2PO_4$, 1.18; $NaHCO_3$, 25.00; glucose, 11.66 and $CaCl_2$, 1.25 gassed with a mixture of 95% $O_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platinum or silver electrodes placed on opposite sides of the tissue. Electrodes are made from 2-gauge silver wire wound into a tight coil approximately 12–14 mm in diameter. Electrodes are connected to a Grass stimulator via Grass constant current unit. Tissues are driven at 90 pulses per minute with 5 msec duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions calculated via the method of Finney (1971) are compared using Student's t-test.

The following in vitro method is another means for measuring the inotropic potency of the present compounds. This method is a modification of the enzyme inhibition method reported by Thompson and Appleman (1970) and Thompson et al. (1974), and is believed to correlate to in vivo inotropic activity in humans.

Inhibition of Peak III cAMP Phosphodiesterase Activity

The test compounds are included in media comprising a radioactivity labeled substrate ($^3$H-cyclic nucleotide) such as adenosine 3':5'-monophosphate (cyclic AMP) and quanine-3':5'-nucleotidease isolated from a dog heart. The inhibition of the enzyme hydrolysis of the 5'-nucleotide product of the cNUC-PDEase to the corresponding nucleoside is measured by separating the charged, unhydrolyzed substrate from the uncharged hydrolysis product. Separation may be achieved either chromatographically from the uncharged nucleoside product of the assay with ionexchange resin so that it is not quantitated with the liquid scintillation counter.

Anesthetized Dog Procedure

Male mongrel dogs are anesthetized with pentobarbital (35 mg/kg, i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastolic pressure and dP/dt. Lead II ECG and heart rate are also monitored. All parameters are measured on a Beckman Dynagraph.

Two additional test procedures which have been found to be an efficient means for ascertaining the inotropic activity of the compounds of this invention are described below.

Conscious Instrumented Dog

Female mongrel dogs (18.0–18.5 kg) are anesthetized with sodium pentobarbital (35 mg/kg, i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with haparinized 50% dextrose solution, and the chest is closed and evacuated.

The dogs are treated daily post-operatively with 600,000 units of penicillin-procaine i.m. for ten days and with chloramphenicol, 500 mg/kg, i.m., every other day for 10 days and allowed at least 7 days recovery before use.

Each dog is trained and acclimated to its environment and the presence of personnel during the experiment.

The dogs are fasted overnight before either intravenous or oral administration of the compound. On a test day, the dog is placed in a sling and connected to a recorder (Gould Instruments or Grass Instruments) for measurement of left ventricular pressure, left ventricular $dP/dt_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl; sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The acqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic resonse until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age and other factors which may influence response to the drug. The drug may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally 1 to 4 times per day. It is anticipated that many patients will require no more than about one to about two doses daily.

It is also anticipated that the present invention would be useful as an injectable dosage form which may be administered in an emergency to a patient suffering from acute cardiac failure. Such treatment may be followed by intravenous infusion of the active compound and the amount of compound infused into such a patient should be effective to achieve and maintain the desired therapeutic response.

Compounds of this invention may be prepared by the following examples.

EXAMPLE 1

6-(3-CYANO-6-METHYL-2-OXO-1,2-DIHYDROPYRIDIN-5-YL)-3,4-DIHYDRO-3-METHYL-1H-QUINAZOLIN-2-ONE

Step 1. 6-(2-bromopropionyl-3,4-dihydro-3-methyl-2(1H)quinazolinone

2-Bromopropionyl bromide (71.02 g) is added dropwise to a stirred mixture of 3,4-dihydro-3-methyl-2(1H)quinazolinone (26.75 g) and anhydrous aluminum chloride (54.98 g) in carbon disulfide (350 ml). The reaction mixture is stirred under reflux for 5 hrs., the carbon disulfide decanted, and the residue treated with HCl (6N). The resulting solid is filtered, and washed with water and dried in vacuo to obtain 6-(2-bromopropionyl)-3,4,dihydro-3-methyl-2(1H)-quinazolinone which is used in the next step.

Step 2. 6-(2-acetoxypropionyl)-3,4-dihydro-3-methyl-2(1H)-quinazolinone

A mixture of 6-(2-bromopropionyl)-3,4-dihydro-3-methyl-2(1H)-quinazolinone (2 g) prepared in Step 1, potassium acetate (2.64 g) and glacial acetic acid (20 ml) is refluxed for three hours. The reaction mixture is diluted with water and extracted with methylene chloride (3×50 ml) and the combined organic layers are washed with saturated aqueous sodium bicarbonate, dried, filtered and concentrated to obtain 6-(2-acetoxypropionyl)-3,4-dihydro-3-methyl-2(1H)-quinazolinone which is used in the next step.

Step 3. 6-(2-acetoxy-1-hydroxypropyl)-3,4,dihydro-3-methyl-2(1H)-quinazolinone

Sodium borohydride (0.1 g) added slowly to a cooled stirred solution of 6-(2-acetoxypropionyl)-3,4-dihydro-3-methyl-2(1H)-quinazolinone (1.0 g) prepared in Step 2 in 25 ml diglyme. The mixture is allowed to warm to room temperature and stirred for one hour. The reaction mixture is cooled to 0° C., 1.5 g $KHSO_4$ is added slowly, stirred for about 5 min. and 1 g $KHSO_4$ in 50ml $H_2O$ added. The mixture is then extracted with ethyl acetate(3×50 ml). The organic extract is washed with saturated aqueous sodium bicarbonate, dried, filtered and concentrated by vacuum distillation to obtain a viscous yellow oil which NHR indicates to be the desired 6-(2-acetoxy-1-hydroxypropyl)-3,4-dihydro-3-methyl-2(1H)-quinazolinone which is used in the next step.

Step 4. 6-(2-oxopropyl)-3,4-dihydro-3-methyl-2(1H)-quinazolinone

A mixture of 6-(2-acetoxy-1-hydroxypropyl)-3,4-dihydro-3-methyl-2(1H)-quinazolinone (6.47 g) prepared in Step 3 and potassium bisulfate (4.75 g) are ground together and placed under aspirator vacuum in an oil bath at 170° C. until all the material is a melt. Upon cooling the residue is partioned between methylene chloride (100 ml) and water (50 ml). The aqueous is diluted with 50 ml sat. sodium bicarbonate solution and sodium chloride (30 g) and then extracted with methylene chloride. The combined methylene chloride extracts are washed with sat. sodium bicarbonate, sat. aqueous sodium chloride solution, dried over $Na_2SO_4$, filtered and evaporated in vacuo. The residue dissolved in 5% methanol in chloroform was purified using flash chromotography on a silica gel column (230–400 mesh) to obtain pure 6-(2-oxopropyl)-3,4-dihydro-3-methyl-2(1H)-quinazolinone which was used in the next step.

Step 5. 6-[2-(1-dimethylamino-3-oxo-1-butene-2-yl)]-3,4-dihydro-3-methyl-2(1H)-quinazolinone A mixture of 6-(2-oxopropyl)-3,4-dihydro-3-methyl-2(1H)-quinazolinone (1.4 g), dimethylformamide dimethyl acetal (20 ml) and pyridine (5 drops) are heated at 80° C. for 1¼ hrs. The reaction mixture is cooled to room temperature, filtered and washed with a few ml. of DMF-DMA, ether and then air dried to obtain 6-[2-(1-dimethylamino-3-oxo-1-butene-2-yl)]-3,4-dihydro-3-methyl-2(1H)-quinazolinone (m.p. 228°–232° C).

Step 6. 6-[3-cyano-6-methyl-2-oxo-1,2-dihydropyridin-5-yl]-3,4-dihydro-3-methyl-2(1H)-quinazolinone A mixture of 6-[2-(1-dimethylamino-3-oxo-1-butene-2-yl)]-3,4-dihydro-3-methyl-2(1H)-quinazolinone (840 mg) from Step 5, 2-cyanoacetamide (284 mg), sodium hydride (oil-free) (193 mg), and anhydrous DMF (10 ml) is stirred under nitrogen and maintained at about 80° C. for about 4 hrs. The reaction mixture is then allowed to stir at room temperature overnight. The mixture is added to 40 ml of 20% ammonium chloride solution, filtered and the solid washed with water and dried in vacuo affording crude solid. Upon recrystallization using warm DMF and a mixture of methylene chloride and hexane (1:1) the 6-[3-cyano-6-methyl-2-oxo-1,2-dihydro-pyridin-5-yl]-3,4-dihydro-3-methyl-2(1H)-quinazolinone is obtained as a solid [m.p.>350° C. (dec.)]

Calculated: C=65.29; H=4.79; N=19.04. Found: C=64.92; H=5.17; N-19.02.

EXAMPLE 2

When bromoacetyl chloride is used in place of 2-bromopropionyl bromide in Step 1 of Example 1 then the product obtained is 6-[3-cyano-2-oxo-1,2-dihydropyridin-5-yl]-3,4-dihydro-3-methyl-2(1H)-quinazolinone.

EXAMPLE 3

When N-methyl-2-cyanoacetamide is used in place of 2-cyanoacetamide in Step 6 of Example 1 then the product obtained is 6-[3-cyano-1,6-dimethyl-2-oxo-1,2-dihydropyridin-5-yl]-3,4-dihydro-3-methyl-2(1H)-quinazolinone.

EXAMPLE 4

When the procedure of Examples 1-3 are followed and the 3,4-dihydro-3-methyl-2(1H)-quinazolinone of Step 1 is replaced by the compounds of Table I below, then the corresponding representative products of Table II below are obtained.

TABLE I 3,4-dihydro-2(1H)-quinazolinone
3,4-dihydro-1-methyl-2(1H)-quinazolinone
3,4-dihydro-4-methyl-2(1H)-quinazolinone
3,4-dihydro-1,3-dimethyl-2(1H)-quinazolinone
3,4-dihydro-1,4-dimethyl-2(1H)-quinazolinone
3,4-dihydro-3-ethyl-2(1H)-quinazolinone
3,4-dihydro-3-benzyl-2(1H)-quinazolinone
3,4-dihydro-2(1H)-quinoxalinone
3,4-dihydro-1-methyl-2(1H)-quinoxalinone
3,4-dihydro-3-methyl-2(1H)-quinoxalinone
3,4-dihydro-4-methyl-2(1H)-quinoxalinone
2-oxo-1,3-dihydrobenzimidazole
1-methyl-2-oxo-1,3-dihydrobenzimidazole
2-oxo-1,3,4,5-tetrahydro-1,3-benzodiazepine
1-methyl-2-oxo-1,3,4,5-tetrahydro-1,3-benzodiazepine
3-methyl-2-oxo-1,3,4,5-tetrahydro-1,3-benzodiazepine
4-methyl-2-oxo-1,3,4,5-tetrahydro-1,3-benzodiazepine
5-methyl-2-oxo-1,3,4,5-tetrahydro-1,3-benzodiazepine 2-oxo-1,3,4,5-tetrahydro-1,4-benzodiazepine
2-oxo-1,3,4,5-tetrahydro-1,5-benzodiazepine
2-oxo-1,3-dihydro-1,3-benzodiazepine
2-oxo-1,5-dihydro-1,5-benzodiazepine

TABLE II 6-(3-cyano-6-methyl-2-oxo-1,2-dihydropyridin-5-yl)-3,4-dihydro-2(1H)-quinazolinone
6-(3-cyano-6-methyl-2-oxo-1,2-dihydropyridin-5-yl)-3,4-dihydro-1-methyl-2(1H)-quinazolinone
6-(3-cyano-6-methyl-2-oxo-1,2-dihydropyridin-5-yl)-3,4-dihydro-4-methyl-2(1H)-quinazolinone
6-(3-cyano-6-methyl-2-oxo-1,2-dihydropyridin-5-yl)-3,4-dihydro-1,3-dimethyl-2(1H)-quinazolinone
6-(3-cyano-6-methyl-2-oxo-1,2-dihydropyridin-5-yl)-3,4-dihydro-1,4-dimethyl-2(1H)-quinazolinone
6-(3-cyano-6-methyl-2-oxo-1,2-dihydropyridin-5-yl)-3,4-dihydro-3-ethyl-2(1H)-quinazolinone
6-(3-cyano-6-methyl-2-oxo-1,2-dihydropyridin-5-yl)-3,4-dihydro-3-benzyl-2(1H)-quinazolinone
6-(3-cyano-6-methyl-2-oxo-1,2-dihydropyridin-5-yl)-3,4-dihydro-2(1H)-quinoxalinone
7-(3-cyano-6-methyl-2-oxo-1,2-dihydropyridin-5-yl)-3,4-dihydro-2(1H)-quinoxalinone
6-(3-cyano-6-methyl-2-oxo-1,2-dihydropyridin-5-yl)-3,4-dihydro-1-methyl-2(1H)-quinoxalinone
7-(3-cyano-6-methyl-2-oxo-1,2-dihydropyridin-5-yl)-3,4-dihydro-1-methyl-2(1H)-quinoxalinone
6-(3-cyano-6-methyl-2-oxo-1,2-dihydropyridin-5-yl)-3,4-dihydro-3-methyl-2(1H)-quinoxalinone
6-(3-cyano-6-methyl-2-oxo-1,2-dihydropyridin-5-yl)-3,4-dihydro-4-methyl-2-(1H)-quinoxalinone
5-(3-cyano-6-methyl-2-oxo-1,2-dihydropyridin-5-yl)-2-oxo-1,3-dihydrobenzimidazole
5-(3-cyano-6-methyl-2-oxo-1,2-dihydropyridin-5-yl)-1-methyl-2-oxo-1,3-dihydrobenzimidazole
6-(3-cyano-6-methyl-2-oxo-1,2-dihydropyridin-5-yl)-1-methyl-2-oxo-1,3-dihydrobenzimidazole
7-(3-cyano-6-methyl-2-oxo-1,2-dihydropyridin-5-yl)-2-oxo-1,3,4,5-tetrahydro-1,3-benzodiazepine
7-(3-cyano-6-methyl-2-oxo-1,2-dihydropyridin-5-yl)-1-methyl-2-oxo-1,3,4,5-tetrahydro-1,3-benzodiazepine
7-(3-cyano-6-methyl-2-oxo-1,2-dihydropyridin-5-yl)-2-oxo-3-methyl-1,3,4,5-tetrahydro-1,3-benzodiazepine
7-(3-cyano-6-methyl-2-oxo-1,2-dihydropyridin-5-yl)-2-oxo-4-methyl-1,3,4,5-tetrahydro-1,3-benzodiazepine
7-(3-cyano-6-methyl-2-oxo-1,2-dihydropyridin-5-yl)-2-oxo-5-methyl-1,3,4,5-tetrahydro-1,3-benzodiazepine
7-(3-cyano-6-methyl-2-oxo-1,2-dihydropyridin-5-yl)-2-oxo-1,3,4,5-tetrahydro-1,4-benzodiazepine
7-(3-cyano-6-methyl-2-oxo-1,2-dihydropyridin-5-yl)-2-oxo-1,3,4,5-tetrahydro-1,5-benzodiazepine
5-(3-cyano-2-oxo-1,2-dihydropyridin-5-yl)-1-methyl-2-oxo-1,3-dihydrobenzimidazole
5-(3-cyano-1,6-dimethyl-2-oxo-1,2-dihydropyridin-5-yl)-1-methyl-2-oxo-1,3-dihydrobenzimidazole
6-(3-cyano-1,6-dimethyl-2-oxo-1,2-dihydropyridin-5-yl)-1-methyl-2-oxo-1,3-dihydrobenzimidalole
7-(3-cyano-2-oxo-1,2-dihydropyridin-5-yl)-2-oxo-1,3,4,5-tetrahydro-1,3-benzodiazepine
7-(3-cyano-6-methyl-2-oxo-1,2-dihydropyridin-5-yl)-2-oxo-1,3-dihydro-1,3-benzodiazepin
7-(3-cyano-6-methyl-2-oxo-1,2-dihydropyridin-5-yl)-2-oxo-1,5-dihydro-1,5-benzodiazepine.

We claim:

1. A compound of the formula:

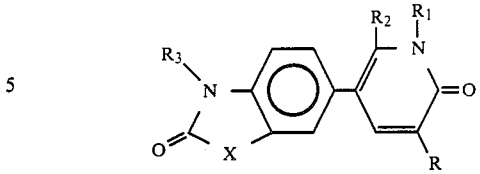

where
R is
  hydrogen
  alkyl having 1 to 6 carbon atoms
  alkoxyalkyl wherein alkoxy has 1 to 6 carbon atoms and alkyl has 1 to 6 carbon atoms
  hydroxyalkyl having 1 to 6 carbon atoms
  halo
  cyano
  carbamoyl
  alkyl carbamoyl wherein alkyl has 1 to 6 carbon atoms
  formyl
  alkyleneamino having 1 to 6 carbon atoms or
  amino;
X is $$-(CR_4R_5)_a-\underset{R_6}{N}-(CR_4R_5)_b-;$$

$R_1$, $R_2$, $R_3$, and $R_5$ are
  hydrogen or
  alkyl having 1 to 6 carbon atoms;
$R_4$ and $R_6$ are
  hydrogen
  alkyl having 1 to 6 carbon atoms or
  benzyl or phenethyl
a and b are 0, 1 or 2 and a+b=0, 1 or 2;
$R_4$ or $R_5$ groups on vicinal carbon atoms may together form a carbon-carbon double bond; and geminal $R_4$ and $R_5$ groups may together form a spiro substituent, $-(CH_2)_d-$, where d is 2 to 5; or a pharmaceutically acceptable salt thereof.

2. A compound according to claim 1 where R is cyano.

3. A compound according to claim 2 where $R_1$ is hydrogen.

4. A compound according to claim 3 where $R_2$ is lower alkyl.

5. A compound according to claim 4 where $R_2$ is methyl.

6. A compound according to claim 5 where $R_3$ is hydrogen.

7. A compound according to claim 6 where X is $$-(CR_4R_5)_a-\underset{R_6}{N}-$$

and a is 1 or 2.

8. A compound according to claim 6 where X is $$-\underset{R_6}{N}-(CR_4R_5)_b-$$

and b is 1 or 2.

9. A compound according to claim 7 where a is 1.

10. A compound according to claim 6 where a is 1 and b is 1.

11. A compound according to claim 6 where a is 0 and b is 0.

12. A compound according to claim 8 where b is 1 and $R_4$, $R_5$ and $R_6$ are hydrogen or methyl.

13. A compound according to claim 8 where b is 2 and $R_4$, $R_5$ and $R_6$ are hydrogen or methyl.

14. A compound according to claim 12 where $R_4$ and $R_5$ are hydrogen and $R_6$ is methyl thus forming 6-(3-cyano-6-methyl-2-oxo-1,2-dihydropyridin-5-yl)-3,4-dihydro-3-methyl-1H-quinazolin-2-one.

15. A compound according to claim 13 where $R_4$ and $R_5$ are hydrogen and $R_6$ is methyl.

16. A compound according to claim 10 where $R_4$ and $R_5$ are hydrogen and $R_6$ is methyl.

17. A compound according to claim 11 where $R_6$ is methyl thus forming 5-(3-cyano-6-methyl-2-1,2-dihydropyridin-5-yl)-1-methyl-2-oxo-1,2-dihydrobenzimidazole.

18. A compound according to claim 11 where $R_6$ is hydrogen, thus forming 5-(3-cyano-6-methyl-2-oxo-1,2-dihydropyridin-5-yl)-2-oxo-1,3-dihydrobenzimidazole.

19. A compound according to claim 12 where $R_4$, $R_5$ and $R_6$ are hydrogen.

20. A method for increasing cardiotonic contractility in a patient requiring such treatment which comprises administering to such patient an effective amount of a compound according to claim 1.

21. A pharmaceutical composition for increasing cardiotonic contractility in a patient requiring such treatment comprising an effective amount of a compound according to claim 1 in admixture with a pharmaceutically acceptable carrier.

* * * * *